(12) United States Patent
McClory et al.

(10) Patent No.: US 7,803,409 B2
(45) Date of Patent: Sep. 28, 2010

(54) **USE OF NATURALLY OCCURRING EPOXIDISED MOLECULES FROM *VERNONIA GALAMENSIS***

(75) Inventors: Paul G. McClory, Churchill (GB); Anthony Atkinson, Salisbury (GB)

(73) Assignee: Vernolix Limited, London (GB)

( * ) Notice: Subject to any disclaimer, the term of this patent is extended or adjusted under 35 U.S.C. 154(b) by 0 days.

(21) Appl. No.: 11/650,205

(22) Filed: Jan. 3, 2007

(65) Prior Publication Data

US 2007/0202207 A1    Aug. 30, 2007

(51) Int. Cl.
*A61K 36/00* (2006.01)

(52) U.S. Cl. .................................................. 424/725

(58) Field of Classification Search ........................ None
See application file for complete search history.

(56) References Cited

U.S. PATENT DOCUMENTS

| 5,676,935 A | 10/1997 | Mellul et al. |
| 5,693,327 A | 12/1997 | Shah |
| 6,180,668 B1 * | 1/2001 | O'Lenick et al. ............ 514/547 |
| 6,346,539 B1 | 2/2002 | Raman et al. |
| 6,680,391 B2 | 1/2004 | Raman et al. |
| 2005/0118248 A1 | 6/2005 | Grinberg et al. |

FOREIGN PATENT DOCUMENTS

| DE | 91617 | 10/1969 |
| EP | 1297832 A2 | 4/2003 |
| EP | 1297832 A3 | 4/2003 |
| EP | 1198237 | 6/2004 |
| GB | 1335867 | 10/1973 |
| GB | 2353706 | 3/2001 |
| WO | WO02/055011 | 7/2002 |
| WO | WO03/047499 | 6/2003 |
| WO | WO2005/079823 | 9/2005 |

OTHER PUBLICATIONS

CIted by Applicants. Johri et al.: Medicinal Uses of *Veronia* Species.: Journal of Medicinal and Aromatic Plant Sciences. 19 (1997) 744-752).*
Tasake et al.: Intraarticular Lesions in Traumatic Anterior Shoulder Instability. Acta Orthopaedica. 20005; 76 (6): 854-857.*
Ulcer. Achcive date Nov. 27, 2004. Retrieved from the internet <http://web.archive.org/web/20041127184347/http://en.wikipedia.org/wiki/Ulcer> Retrieved on May 23, 2008.*
Chemical compound. retrieved from the internet. <http://en.wikipedia.org/wiki/Chemical_compound>. Retrieved on Jun. 19, 2009.*
Manjunatha, B.K. et al., "Evaluation of Wound-Healing Potency of *Vernonia Arborea* HK", Medicinal & Aromatic Plants Abstracts, National Institute,p. 223-226, V. 37, No. 4, 2005.
Johri, R.K. et al., "Medicinal Uses of *Vernonia* Species", Journal of Medicinal and Aromatic Plant Sciences, p. 744-752, V.19, 1997.
Teynor, T.M. et al., "Alternative Field Crops Manual, *Vernonia*", Univ. Wisconsin, Univ. Minnesota, p. 1-5, 1992.
Leite, S.N. et al., "Wound Healing Activity and Systemic Effects of *Vernonia Scorpioides* Extract in Guinea Pig", Fitoterapia, p. 496-500, V. 73, 2002.
Gunstone, F.D., "The Nature of the Oxygenated Acid Present in *Vernonia Anthelmintica* (Willd.) Seed Oil", British Library, Part II, p. 1611-1616, 1954.
Teynor, T.M. et al., "Alternative Field Crops Manual, Vernonia", Univ. Wisconsin, Univ. Minnesota, p. 1-5, 1992.
Mohamed, Ali I. et al., "Variability in Oil and Vernolic Acid Contents in the New *Vernonia Galamensis* Collection from East Africa", ASHS Press, p. 272-274, 1999.
Baye, Tesfaye et al., "*Vernonia Galamensis*, A Natural Source of epoxy oil", Insutrial Crops and Products, p. 257-261, 2005.
International Search Report in WO2007/077452.
Dahanukar, S.A. et al., "Pharmacology of Medicinal Plants and Natural Products", *Indian Journal of Pharmacology*, 32, S81-S118 (2000).
Stedman's Medical Dictionary, 26th Edition, (1995).
Johri, R.K. et al., "*Vernonia lasiopus* and *Vernonia galamensis*: A medicinal perspective", Research and Industry, p. 327-328, V.40, Dec. 1995.

\* cited by examiner

*Primary Examiner*—Patricia Leith
*Assistant Examiner*—Melenie McCormick
(74) *Attorney, Agent, or Firm*—Koppel, Patrick, Heybl & Dawson; Michael J. Ram

(57) ABSTRACT

Epoxidised oil, epoxidised wax or epoxidised fatty acid ester recovered from *Vernonia Galamensis* seeds provide topical medicament preparations which are effective in preventing and treating various different forms of skin diseases, skin lesions and wounds. These epoxidised oil, epoxidised wax or epoxidised fatty acid ester recovered from *Vernonia Galamensis* seeds can also be bound to bio-available molecules, such as proteins, to modify the effect of the bio-available molecules when administered to the human body.

6 Claims, 3 Drawing Sheets
(3 of 3 Drawing Sheet(s) Filed in Color)

USE OF NATURALLY OCCURRING EPOXIDISED MOLECULES FROM *VERNONIA GALAMENSIS*

This application claims benefit of British Patent Application GB0600134.1, filed Jan. 5, 2006.

The invention relates to the use of epoxidised compounds such as oils, esters and waxes. A particularly preferred epoxidised compound is vernonia oil. More particularly, the vernonia oil is obtained from the seed of *Vernonia Galamensis*.

BACKGROUND

*Vernonia* oil is an inedible oil which may be derived from various different plants classified within genus *vernonia* in the family asteraceae (Compositea). There are over 1000 different species in genus *Vernonia* with numerous different varieties, in the form of trees, bushes or flowering weeds. Various varieties and parts of the plants have been used in folk medicine around the world. The properties of a particular variety do not appear to be exhibited by all of the *vernonia* plants and it has been found that each variety must be individually evaluated as to its particular uses or benefits. Most of the applications are based on ingestion of extracts, teas or whole or powdered parts (leaves, bark, roots) of the tree, bush or weed. These applications include a broad range of intestinal or gastric problems (stomach ache, cramps, digestive aid, appetite stimulant, nausea, diuretic, laxative, ulcers, purgative, gastritis, enteritis, colic, dysentery) venereal diseases or genital problems (gonorrhea, impotence, metrorrhagia, regulate menses, labor pain, reproductive problems, relief, abortifacient, aphrodisiac, lactogogue) infection, convulsions and spasms, common cold, pneumonia, cough, fever, malaria, bleeding, hemorrhage, epistaxis, anemia, diabetes, kidney problems and metabolic diseases associated with the liver, ringworm, vermifuge, cholera, scurvy, yaws, mange, sprue, snake bite, asthma, headache, night blindness and for certain varieties as a topical treatment for the skin, sores and wounds (*V. arborea*, *V. amygdalina*, *V. kotshyana*, *V. missurica*, *V.* Sp, *V. teres*). It has also been reported that *vernonia anthelminticum* contains a chemical that may be effective in treating psoriasis. However, the fact that a particular variety has been suggested in folk medicine for a particular condition does not mean that it is in fact effective for the identified malady, will provide a clinically effective result, or that other plants in the genus *vernonia* will demonstrate the asserted function.

*V. galamensis* (some times referred as *V. pauciflora*) is an annual plant ranging in plant height from 0.2 m to 5.0 m depending on the subspecies and the geographic location. Two centers of diversity are Kenya and northern Tanzania with only one botanical variety occurring outside eastern Africa. *V. galamensis* differs from other annual species of *Vernonia* in leaf form, and/or pappus, and involucre form and size. The seed head (capitula) contains hermaphroditic, protandrous florets.

Oil can be extracted from the seeds of *V. galamensis* using hexane and the fatty acids and glycerides can then be removed from the hexane using a solid phase extraction procedure. An aminopropyl phase has been used for the extraction to retain analytes from the non-polar matrix through interactions between the amino groups on the modified silica surface and the carbonyl groups on the fatty acids and glycerides. For the elution step, advantage is taken of the differences in the lipophilic character between the fatty acids and the glycerides by eluting each of these fractions with solvents of different polarity.

Like other vegetable oils, *vernonia* oil is a mixture of glycerides, mainly triglycerides, a combination of three fatty acids esterified to a glycerol molecule. The principal fatty acid in *vernonia* oil is vernolic acid, a naturally occurring epoxidised fatty acid. Two species have been primarily identified as a source of epoxidized oils for various different industrial applications, *Vernonia Galamensis* and *Vernonia Anthelminticum*. The vernolic acid in *vernonia* oil recovered from these species is a commercially important epoxy fatty acid because it is easily polymerized. It is useful for metal coatings, and as a diluent for alkyd paints, in plasticizers, adhesives, synthetic fibers and plastics. The *vernonia* oil is of a higher quality then epoxidized linseed and soybean oils that are currently used for these applications.

WO 02/055011, published in the U.S. on Jun. 2, 2005 as U.S. 2005/0118248 describes the use of amphiphilic derivatives having at least one fatty acid chain derived from vegetable oils, such as *vernonia* oil, in the production of vesicles, micelles and complexants. WO 03/047499 describes the use of ampiphilic compounds to form vesicles or liposomes for use in drug targeting. The particular source of *vernonia* oil was not indicated and *Vernonia Galamensis* as a source is not mentioned. Also, no mention was made in these publications of the medicinal benefits of *vernonia* oil, the application described being the formation of vesicles to carry other medicinal compounds.

U.S. Pat. No. 6,680,391, to Raman et al, as well as other patents by the same inventors, mentions that preparations from *vernonia anthelminticum* has been used in folk medicine for the treatment of vertiligo. Several patents issued to Deckers et al, of which U.S. Pat. No. 6,599,513 is one example, are directed to topical emulsions in which oil from *Vernonia Galamensis* is listed, along with many other plant sources of oils, for forming the emulsions. While these emulsion are said to be usable in personal care and dermatological products there is no mention of any particular therapeutic benefits, the oils merely serving as carriers for other materials. Numerous other patents also mention vernonia oil, along with other plant derived oils as ingredients in various compositions or as a reactant in industrial products. Again, no therapeutic benefits are suggested.

The seeds of both *Vernonia anthelminticum* and *Vernonia galamensis* are about 40% oil. EP-A-1198237 discloses the use of extracts derived from the seeds of *Centratherum anthelminticum* (also known as *Vernonia anthelmintica*) for the treatment of skin disorders, such as impetigo and acne, and fungal infections of the skin and nails. U.S. Pat. No. 5,693,327 discloses the use of compositions containing extracts of *Centratherum anthelminticum*, which compositions may be in a form suitable for topical application, for the treatment of psoriasis, eczema and lichen planus. Oil derived from *Centratherum anthelminticum* seed is known to contain significantly less vernolic acid than *Vernonia* Oil (Teymor et al. "*Vernonia*", Alternative Field Crops Manual, updated 26 Jan. 2000, discloses the vernolic acid content of oil derived from *Vernonia galamensis* seed to be about 30% more than the best varieties of *Vernonia anthelmintica*). A typical analysis of the oil is 79-81% vernolic acid, 11-12% linoleic acid, 4-6% oleic acid, 2-3% stearic acid and 2-4% palmitic acid (Ayorinde, F. O. et al. "*Vernonia Galamensis*: A Rich Source of Epoxy Acids", *J. Amer. Oil Chem. Soc.*, 67, p 844 (1990). However, according to the literature these species are very difficult to harvest because the seed pods tend to shatter and scatter the seeds before they can be collected. On the other hand, the leaves of *Vernonia galamensis* have 0.5% or less of vernolic acid.

SUMMARY

The inventors have developed techniques for growing and harvesting the seeds of *Vernonia Galamensis* and discovered that *vernonia* oil and wax recovered from these seeds can be utilised in a number of new and unexpected ways. In particular, the use of an epoxidised oil, epoxidised wax or epoxidised fatty acid ester recovered from *Vernonia Galamensis* seeds provide medicament preparations which are unexpectedly effective in treating various different forms of skin diseases.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Figure 1A:
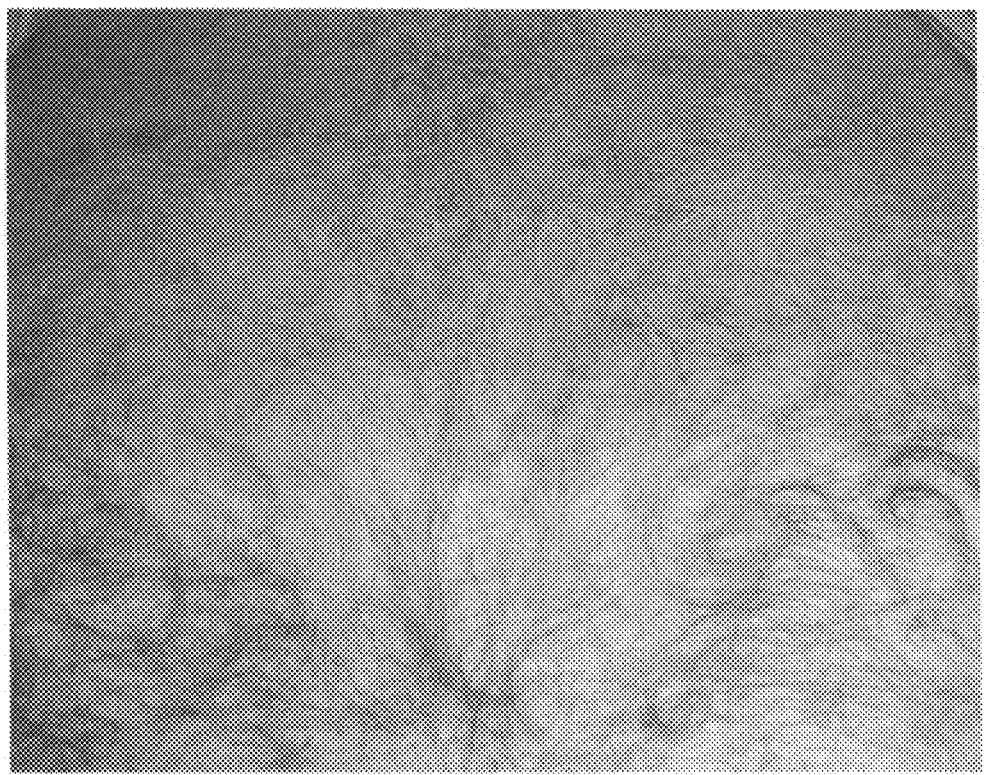
FIGS. 1A and 1B are colored photos of a subject with psoriasis, taken 1 and 8 days, respectively, after beginning treatment with *vernonia* oil obtained from the seeds of *Vernonia Galamensis*.

In a first aspect, the present invention provides the use of an epoxidised compound obtainable by extraction from *Vernonia galamensis* seed in the preparation of a composition for the treatment of a lesion on the skin of a mammal. Preferably, the treatment is by topical administration of the composition onto the lesion.

In another aspect, the present invention provides an emollient composition comprising an epoxidised compound obtainable by extraction from *Vernonia galamensis* seed. The emollient composition can be used for treating by topical administration a lesion on the skin of a mammal. Alternatively, the emollient composition can be used for the prophylactic treatment by topical administration to the skin of a mammal to prevent or reduce the recurrence of a lesion on the skin.

In another aspect, the present invention provides a dosage form, which may be a botanical drug, comprising a botanical raw material, a botanical drug substance and/or a botanical ingredient from the seed of *Vernonia galamensis*. The terms "drug", "botanical drug", "botanical raw material", "botanical drug substance" and "botanical ingredient" are terms well know to those skilled in the art, but should the reader have any doubt they are referred to their definitions provided in WO-A-05079823, which definitions are incorporated herein by reference.

In another aspect, the present invention provides a method of treating a lesion on the skin of a mammal by administering to the mammal an epoxidised compound obtainable by extraction from *Vernonia galamensis* seed.

In another aspect, the present invention provides a method of treating the skin of a mammal to prevent or reduce the recurrence of a lesion on the skin of a mammal by the prophylactic administration of an emollient composition comprising an epoxidised compound obtainable by extraction from *Vernonia galamensis* seed.

In one embodiment of the above aspects, the skin lesion may be caused by a skin disease. The disease may be an infection, such as a bacterial infection, viral infection or fungal infection. Examples such a skin disease include psoriasis, dermatitis, ulceration or eczema.

In another embodiment of the above aspects, the lesion is a wound, such as a graze, cut, scratch or burn.

The lesion may be an inflammation of the skin, such as may be caused by an infection or by a wound such as a burn.

In another aspect, the present invention provides a protein having at least one epoxidised oil, epoxidised wax or epoxidised fatty acid ester bound to it. Preferably, the at least one epoxidised oil, wax or fatty acid ester is obtainable by extraction from *Vernonia galamensis* seed.

In other aspects, the present invention provides methods of changing the i) size, ii) the immunogenecity or iii) the biological half life of a protein. In each of these aspects, the method comprises bonding at least one epoxidised oil, epoxidised wax or epoxidised fatty acid ester to the protein.

In another aspect, the present invention provides a compound comprising a bio-available molecule bonded to at least one epoxidised oil, epoxidised wax or epoxidised fatty acid ester. Preferably, the at least one epoxidised oil, wax or fatty acid ester is obtainable by extraction from *Vernonia galamensis* seed.

In yet another aspect, the present invention provides a method of preparing a bio-available compound in a slow-release format, comprising bonding the bio-available compound to at least one epoxidised oil, epoxidised wax or epoxidised fatty acid ester.

In each of the above aspects, the epoxidised compound, oil, ester or wax is preferably obtained from *Vernonia galamensis* seed. For example, the epoxidised compound, oil, ester or wax is as found naturally in *Vernonia* oil obtained from *Vernonia galamensis* seed.

In another aspect, the present invention provides the use of an epoxidised compound obtainable by extraction from *Vernonia* plants in the preparation of a composition for the treatment of a lesion on the skin of a mammal, wherein the lesion is a wound, such as a graze, cut, scratch or burn. Preferably, the treatment is by topical administration of the composition onto the lesion.

In another aspect, the present invention provides an emollient composition comprising an epoxidised compound obtainable by extraction from *Vernonia* plants. The emollient composition can be used for treating by topical administration a lesion on the skin of a mammal, wherein the lesion is a wound, such as a graze, cut, scratch or burn. Alternatively, the emollient composition can be used for the prophylactic treatment by topical administration to the skin of a mammal to prevent or reduce the recurrence of a lesion on the skin originally caused by a wound, such as a graze, cut, scratch or burn.

In another aspect, the present invention provides a method of treating a lesion on the skin of a mammal, wherein the lesion is a wound, such as a graze, cut, scratch or burn, by administering to the mammal an epoxidised compound obtainable by extraction from *Vernonia* plants.

In another aspect, the present invention provides a method of treating the skin of a mammal to prevent or reduce the recurrence of a lesion on the skin of a mammal originally caused by a wound by the prophylactic administration of an emollient composition comprising an epoxidised compound obtainable by extraction from *Vernonia* plants.

In another aspect, the present invention provides a method of treating a lesion on the skin of a mammal, wherein the lesion is a wound, such as a graze, cut, scratch or burn, by administering to the mammal an oil obtainable by extraction from *Vernonia* plants.

In another aspect, the present invention provides a method of treating the skin of a mammal to prevent or reduce the recurrence of a lesion on the skin of a mammal originally caused by a wound by the prophylactic administration of an emollient composition comprising an oil obtainable by extraction from *Vernonia* plants.

In another aspect, the present invention provides the use of an epoxidised compound, such as an epoxidised compound obtainable by extraction from *Vernonia* plants e.g. *Vernonia galamensis* seed, in the preparation of a composition for the treatment by topical administration on a lesion on the skin of a mammal, wherein the lesion is an inflammation, e.g. a burn, and/or is caused by a bacterial, e.g. acne, viral or fungal infection e.g. eczema. The epoxidised compound may be vernolic acid, such as in *Vernonia* oil. The epoxidised compound is preferably in *Vernonia* oil.

In another aspect, the present invention provides a method of treating a lesion on the skin of a mammal wherein the lesion is caused by an inflammation and/or infection of the skin by topical administration of a composition comprising an epoxidised compound. The epoxidised compound may be an epoxidised compound obtainable by extraction from *Vernonia* plants e.g. *Vernonia galamensis* seed. The epoxidised compound may be vernolic acid, such as in *Vernonia* oil. The epoxidised compound is preferably in *Vernonia* oil.

When *vernonia* oil or *Vernonia* oil is used in the present invention, crude vernonia oil or crude Veronia oil may be used, but purified *vernonia* oil or purified *Vernonia* oil may also be used.

Where herein reference is made to a product being "obtainable" from a plant or other named source, the product is preferably "obtained" from that plant or other named source.

The term "oil" as used herein refers to a fixed oil. As such, an oil is a mixture of glycerides, including, for example, triglycerides, diglycerides and monoglycerides. Such an oil may also include a fraction of free fatty acids and glycerol. A glyceride molecule is at least one fatty acid attached to a glycerol molecule. As used herein the term "oil" also encompasses glycerides, that is non-mixed oils composed of a single type of glyceride. The glycerides in an oil are frequently made up of a combination of fatty acids. An epoxidised oil is any oil which contains some glycerides that include a fatty acid containing an epoxy group. The oil may contain more than one type of fatty acid that includes an epoxy group. Preferably, at least 50%, more preferably at least 60%, more preferably at least 70%, more preferably at least 75% and most preferably at least 80% of the fatty acid chains in the oil include an epoxy group. When the term "oil" applies to non-mixed glycerides, the glyceride molecule contains at least one fatty acid containing at least one epoxy group.

The fatty acid including the epoxy group may naturally contain the epoxy group or may have been artificially epoxidised, by changing the fatty acid to make it include at least one epoxy group. The fatty acid may be epoxidised using standard techniques, known to those skilled in the art. Preferably the fatty acid naturally contains an epoxy group. Such fatty acids include, but are not limited to vernolic acid.

The oil is preferably *vernonia* oil obtained from the seeds of *Vernonia Galamensis* referred to as *Vernonia* oil, with a capital "V". *Vernonia* oil is well known in the art and contains vernolic acid as its principal fatty acid. Vernolic acid makes up greater than about 50%, usually about 75 to 80% of the total fatty acids in *vernonia* oil, the remainder being linoleic, oleic and steric acids, depending on the source.

A wax is a fatty acid ester of a long chain monohydroxyl alcohol. An epoxidised wax is a wax in which one or both of the fatty acid and alcohol chains contains at least one epoxy group. Preferably the fatty acid chain contains at least one epoxy group. A wax usually contains a mixture of fatty acid esters of alcohols. It is preferred that all the fatty acid esters in the wax contain an epoxide group. The term "wax" as used also herein includes waxes containing only a single fatty acid ester of a single monohydroxyl alcohol.

An epoxidised wax may be naturally or artificially epoxidised. A naturally epoxidised wax is a wax in which one or both of the fatty acid and alcohol chains naturally contains at least one epoxy group. An artificially epoxidised wax is a wax in which one or both of the fatty acid and alcohol chains has been artificially changed to introduce at least one epoxy group. The ester may be epoxidised using standard techniques, known to those skilled in the art.

The term fatty acid ester means any ester that includes a fatty acid. Examples include methyl, ethyl and propylate esters of a fatty acid. An epoxidised fatty acid ester is one in which the fatty acid contains at least one epoxy group. The fatty acid including the epoxy group may naturally contain the epoxy group or may have been artificially epoxidised, by changing the fatty acid to make it include at least one epoxy group. The fatty acid may be epoxidised using standard techniques, known to those skilled in the art. Preferably the fatty acid naturally contains an epoxy group. Such fatty acids include, but are not limited to vernolic acid.

An epoxy group is a carbon-carbon-oxygen ring and has a structure well known by those skilled in the art. The term is well known in the art, and would be easily understood by a person skilled in the art.

Applicant has discovered that the epoxy group provides epoxidised oils, esters and waxes with very useful properties, such as the ability to bind to proteins, resulting in the compounds being useful for medical uses. It has been found that the epoxidized oil obtained from the seeds of *Vernonia Galamensis* plants has particularly unique medical applications when applied topically to the skin of an individual or an animal. These applications include the treatment of skin diseases and wounds. Skin diseases are disorders that affect the skin, and include, but are not limited to, psoriasis, dermatitis, ulcers and eczema as well as dry scalp and dandruff. It can also alleviate scabies and head lice. *Vernonia* oil from *Vernonia Galamensis* plants is particularly beneficial in the treatment of psoriasis and open wounds.

The invention also provides a method of treating a skin disease, comprising administering an epoxidised oil, epoxidised wax or epoxidised fatty acid ester to a subject in need thereof. Preferably the epoxidised oil, epoxidised wax or epoxidised fatty acid ester is in a pharmaceutically acceptable condition, possibly having been combined with a carrier or vehicle. Preferably the epoxidised oil, epoxidised wax or epoxidised fatty acid ester is prepared for topical administration.

A second aspect of the invention provides the use of an epoxidised oil, epoxidised wax or epoxidised fatty acid ester in the preparation of a medicament for the treatment of a wound. In particular, the medicament is preferably for augmenting the wound healing process. The epoxidised oil, epoxidised wax or epoxidised fatty acid ester is preferably as defined in accordance with the first aspect of the invention. A wound is a break in the structure of an organ or tissue caused by an external agent, including, for example, a graze, a cut, a tear, a puncture and a burn. The medicament is preferably for the treatment of a wound to the skin. The invention also provides a method of treating a wound comprising administering an epoxidised oil, epoxidised wax or epoxidised fatty acid ester to the skin of a subject in need thereof, preferably in a pharmaceutically acceptable condition, possibly having been combined with a carrier or vehicle, for topical administration.

According to a third aspect of the invention, there is provided a protein having at least one epoxidised oil, epoxidised wax or epoxidised fatty acid ester molecule bound to it. Preferably the epoxidised oil, epoxidised wax or epoxidised fatty acid ester is as defined in relation to the first aspect of the invention. Preferably the epoxidised oil, epoxidised wax or epoxidised fatty acid ester is bound to the protein via the epoxy group. Preferably the epoxy group allows bonding to the proteins via a hydroxyl group, a sulphydryl group or an amino group on the protein.

By linking the epoxidised oil, epoxidised wax or epoxidised fatty acid ester to the protein, the protein size may be increased, the immunogenicity of the protein changed, especially lowered, and the potential half-life of the protein, when injected in to the blood stream for example, modified, particularly increased. The protein preferably has one or more epoxidised oil, epoxidised wax or epoxidised fatty acid ester molecule bound to it, most preferably more than six molecules.

A protein is, as is well known in the art, a chain of amino acids. The term protein as used herein includes any length of amino acid chain and encompasses molecules that might otherwise be known as peptides or oligopeptides. The protein according to the invention may be a naturally occurring protein, may be an artificial protein, or may be glycosylated. It is particularly useful if the protein is immunogenic.

The invention also provides a protein having at least one epoxidised oil, epoxidised wax or epoxidised fatty acid ester molecule bound to it for use in therapy. Further provided by the invention is a method of changing the size, immunogenecity or half life of a protein comprising bonding one or more epoxidised oil, epoxidised wax or epoxidised fatty acid ester molecules to the protein under basic catalysis. As used herein, the term "basic catalysis" means that the method is carried out at an alkaline pH, that is a pH of greater than 7. Preferably the pH is between 8 and 12, more preferably 8 and 11, and most preferably between 8.5 and 10.0. It is further preferred that the method is carried out in a non-reactive buffer such as sodium bicarbonate/sodium hydroxide or carbonate.

The epoxidised oil, epoxidised wax or epoxidised fatty acid ester can also be used to modify the size, immunogenicity or half life of a protein. Immunogenicity means the propensity of a protein, or other molecule to generate an immune reaction when it is put into a subject's body. It is particularly useful to be able to modify a protein's immunogenicity, particularly to reduce it, so that useful proteins may be supplied to an individual without a large or deleterious immune reaction being generated.

Biological half-life is a measure of the time a protein, or other molecule remains available to provide its biological effect, for example, when injected into a subject's blood stream. Half-life means the time taken for half of the protein to be broken down.

In a fourth aspect of the invention, there is provided an epoxidised oil, epoxidised wax or epoxidised fatty acid ester bound to a small molecule. By the term "small molecule", we mean a molecule which when introduced into the body is instantly bio-available. It is preferred that the small molecule is a therapeutically useful molecule and can then be used for therapy. Such small bio-available molecules include, but are not limited to, methotrexate, aminopterin, aminosalicylate, doxirubicin. The small bio-available molecule is bonded to the epoxidised oil, wax or ester via the epoxy group. By linking the small molecule to the epoxidised oil, wax or ester, the in use, e.g. in vivo release characteristics of the molecule can be modified. In particular, it is possible to obtain sustained or prolonged release. In the same manner as described above release characteristics of a molecule are modified by bonding the molecule to an epoxidised oil, epoxidised wax or epoxidised fatty acid ester under basic catalysis.

Any small molecule introduced into the body is instantly bioavailable. Covalently bonding it to another molecule such as an epoxidised oil, epoxidised wax or epoxidised fatty acid ester modifies the instant bioavailability so it is not immediately available but comes available as body enzymes hydrolyse the linkage between the oil and the drug.

Without intending to be bound to any extent by this explanation, the inventors believe that the performance of the epoxidised compounds is attributable to the presence of the epoxy group on the vernolic acid per se and/or on epoxidised derivatives of vernolic acid.

*Vernonia* oil may be extracted from *Venonia galamensis* seed by a process involving harvesting the seed and compressing the seed in a press. The oil so obtained may by purified e.g. by filtering to remove solid contaminants, and may be further purified so as to render the oil substantially colourless e.g. by passing through charcoal. The seed may be pressed immediately after harvesting or it may be subjected to one or more treatment steps before pressing. For example, before pressing, the harvested seed may be subjected to a heat treatment, such as by contacting the seed with water at a temperature above 50° C., preferably at boiling, for a period of time sufficient to heat the seed contents to a temperature of more than 50° C., preferably more than 80° C.; and/or the harvested seed may be dried to a water content of 10% by wt or less, based on the weight of seed. In a preferred process, the seed is harvested, contacted with boiling water for a period of at least 15 minutes, e.g. for about an hour, dried to a water content of 6-8 wt %, and then pressed to release the oil.

EXAMPLE 1

Collection and Purification of *Vernonia* Oil

*Vernonia Galamensis* seed is very small having a thickness and length about the same as the lead in a pencil (approximately 0.5-2.0 mm). It has been found that shattering of the seeds (the spontaneous dispersal of mature seed from a plant following ripening) is prevented or significantly reduced by dessicatting (drying out) the crop for thirty (30) days prior to its normal harvest time. The crop is then harvested by cutting into clumps, the clumps being allowed to lie in the fields and dry (swarthing) for an additional month at which time the seeds were harvested using a combine. The seeds were then crushed in an expeller, removing and collecting about 90% of the vernonia oil in the seed. The remaining oil can be recovered by extraction using hexane or other suitable solvents. However, the following procedures and tests were performed on or using the oil recovered by pressing.

*Vernonia Galamensis* seeds obtained as described above were planted in Ethiopia in June, harvested approximately six months thereafter and pressed to recover the *vernonia* oil. 0.5 liters of crude (black) *vernonia* oil obtained by pressing the seeds recovered from *Vernonia Galamensis* were purified by passages through 200 gm of activated charcoal placed in a glass (or plastic) column, the oil being allowed to flow through at about 0.5 l/hr. Complete decolourisation of the yellow effluent can be achieved by re-passage through the same column or an additional column at the same flow rate. The charcoal used was activated charcoal particles typically provided for fish tank filters. However, various different powdered or granulated charcoals or other common color-absorbed materials can be used.

EXAMPLE 2

Wound Healing

An individual received a 14 mm long sharp wound on the left hand across the base of the thumb as a result of an accident with a kitchen knife. The wound was clean and open but despite bandaging failed to close after 48 hours and was still bleeding. Approximately 0.25 ml of refined *vernonia* oil prepared according to Example 1 was rubbed into the wound and the wound re-bandaged for 24 hours. After removal of the bandage it was noted that the wound had begun to "knit" and that the size of the open section had decreased to 8.5 mm. An additional 0.25 ml *vernonia* oil was applied and rubbed in to the wound. The wound was not re-bandaged. After a further 48 hours it was noted that the wound had closed completely and that healing was now proceeding normally. An additional 0.25 ml of *vernonia* oil was applied and rubbed in. Healing was complete, with only a thin silver scar left, within a further 60 hrs.

EXAMPLE 3

Wound Healing

A thumb nail on the right hand of an individual was torn from right to left leaving a 4 mm wound between the nail and the flesh of a subject. Such wounds are difficult to heal, generally taking several weeks. Blood from the wound was removed with cotton pads and the area "patted dry" as much as possible. 0.15 ml of *vernonia* oil prepared in accordance with example 1 was applied to the wound and a bandage placed across the area. After 77 hrs the bandage was removed. The wound had effectively healed. All bleeding had stopped and normal scar lines could be observed. The wound was left open and no complications occurred.

EXAMPLE 4

Wound Healing

Figure 2A:
FIGS. 2A and 2B are colored photos of a subject with wounds, taken on the day the wounds occurred and 9 days after beginning treatment with *vernonia* oil obtained from the seeds of *Vernonia Galamensis*.
Figure 2B:
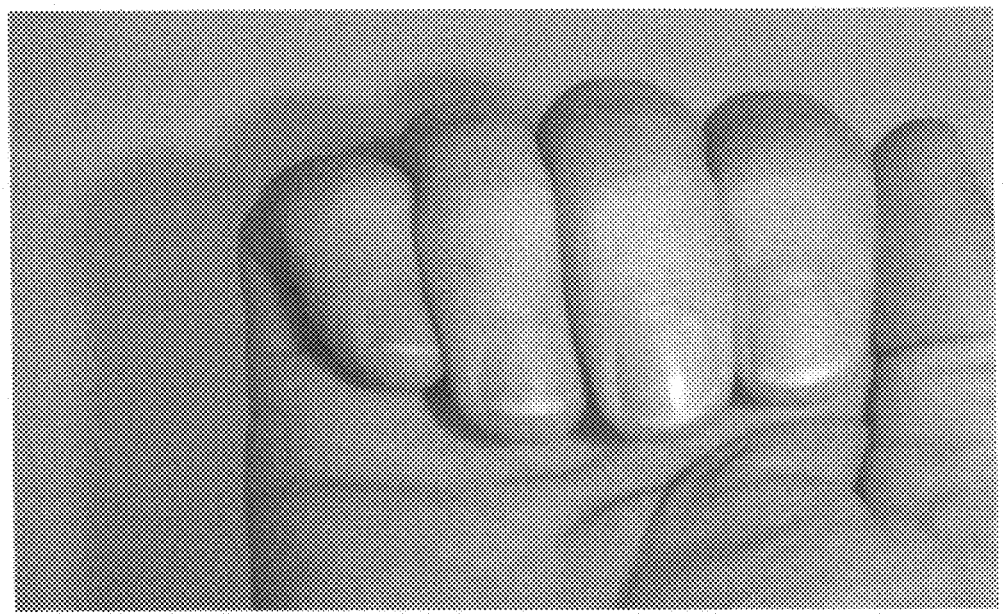

As shown in FIG. 2A, a subject had wounds on two fingers. The subject applied a small amount of *vernonia* oil prepared in accordance with Example 1 once or twice daily for a 9 day period. After 9 days the wounds had healed, as shown in FIG. 2B.

EXAMPLE 5

Healing an Ulcer

Figure 3A:
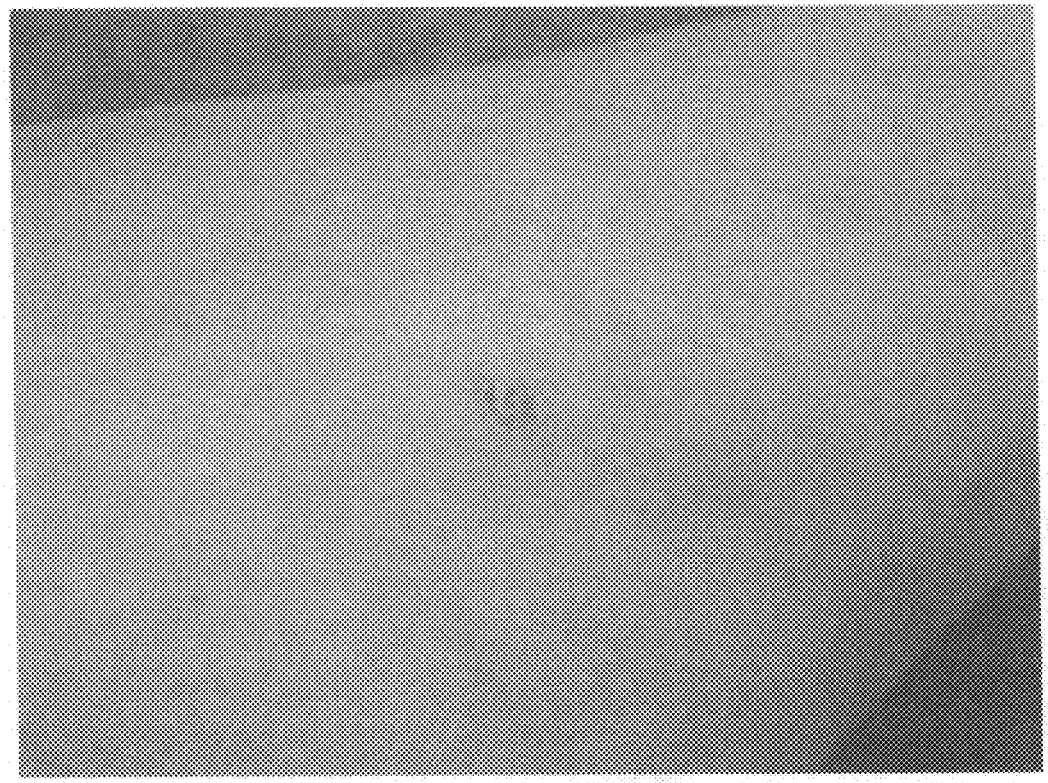
FIGS. 3A and 3B are colored photos of a subject with a skin ulcer, taken on the first day and $11^{th}$ day respectively of treatment with *vernonia* oil obtained from the seeds of *Vernonia Galamensis*.
Figure 3B:
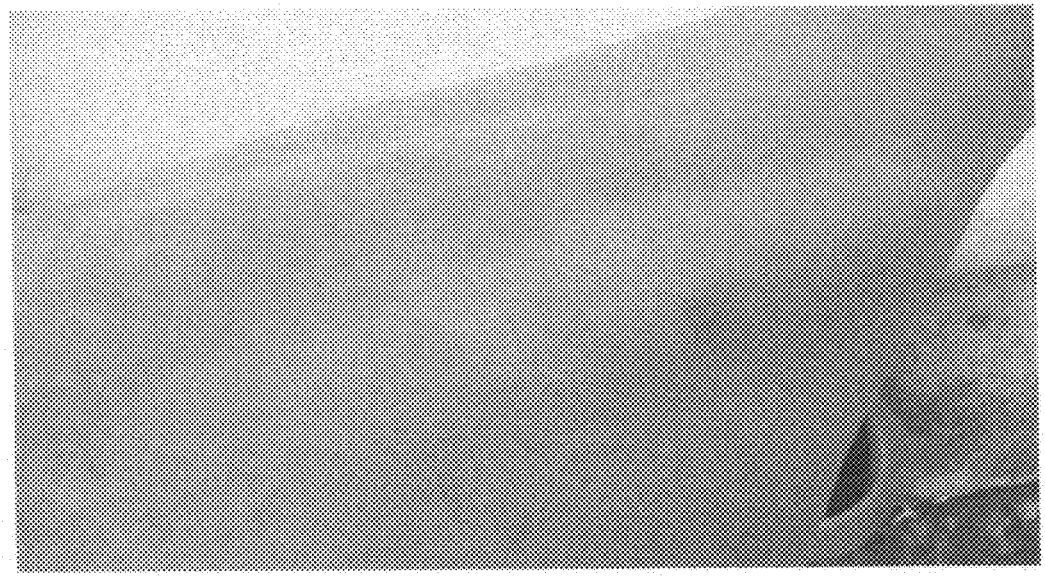

FIG. 3A shows a subject with an ulcer on his leg. A small amount of vernonia oil were applied to the ulcer once or twice daily for a period of 11 days. After 11 days the ulcer had healed, as shown in FIG. 3B.

EXAMPLE 6

Treatment of a Non-Specific Skin Irritation

After a non-specific viral infection itching occurred on both the arms and legs of a subject. Application of known topical medicines, including E45®, Eurax® and use of antihistamine based drugs (Benadryl® and Zirtek®) failed to alleviate the problem. As a result, areas of the arms and legs had become scratched and were raw and irritated. *Vernonia* oil prepared in accordance with example 1 was poured into the palms of the hand and applied as follows:

a) *Vernonia* oil was applied to the broken scratched skin once daily for 3 days. Itching was significantly reduced (from 7 to 3 on a 10 mark scale) and open skin lesions healed rapidly.

b) *Vernonia* oil was applied to unbroken but itching skin. Itching was significantly reduced (from 8 to 2 on a 10 mark scale). Application continued for 4 days. When treatment was stopped no further itching occurred in the affected area.

EXAMPLE 7

Treatment of Psoriasis

Figure 1B:
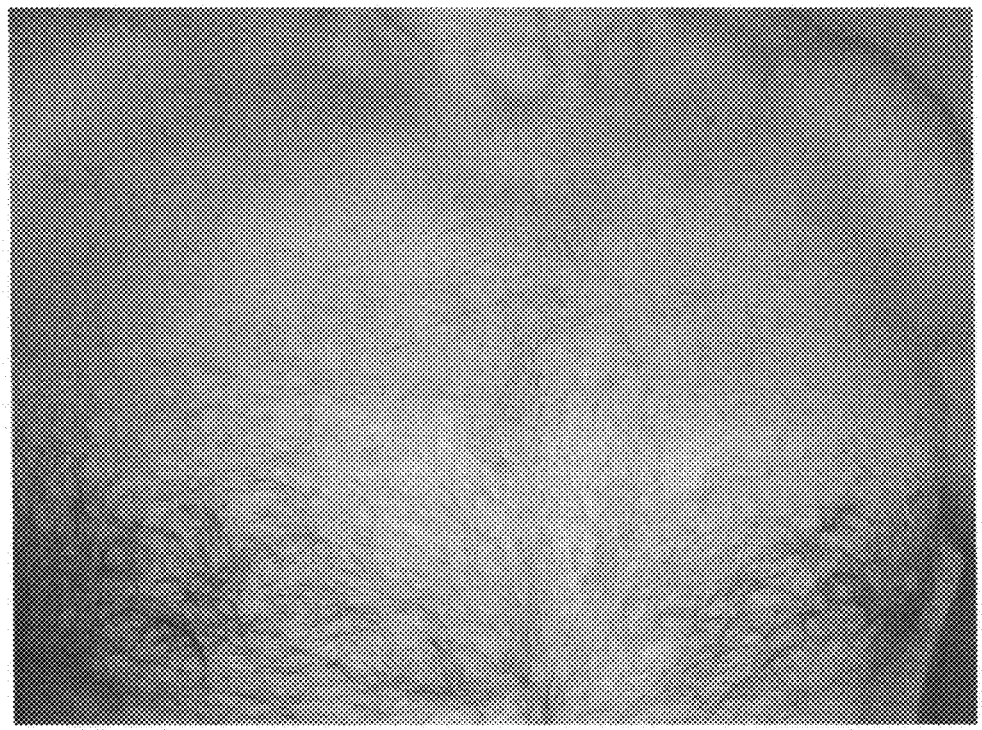

A subject had a mild outbreak of psoriasis on his chest. The subject applied vernonia oil produced in accordance with Example 1 above to the affected area daily. Itching of the area stopped after two days and the psoriasis had virtually disappeared after 8 days. FIGS. 1A and 1B show the psoriasis 1 day and 8 days after the initial application of *vernonia* oil.

The natural epoxide linkage in *vernonia* oil and other epoxidised oils and waxes allows base-catalysed (pH 9.0) bonding of proteins through hydroxyl, sulphydryl or amino groups of proteins such as bovine or human serum albumin (BSA or HSA) HSA, cytochrome C etc. In this way the protein size can be increased, immunogenicity decreased (through "cloaking" and subsequent reduction in opsonisation (the process of coating micro-organisms with plasma proteins)) and the potential half life of a protein injected into the blood stream can be modified. Steric calculations indicate that about 2 to 4 triglyceride molecules could be bonded onto an average of 35,000 dalton protein chain. Base-catalysed reaction of *vernonia* oil with BSA indicates that the protein molecule size increases (as determined by HPLC) from about 67,000 dalton to about 75,000 dalton indicating some 7 to 8 triglyceride molecules per 67,000 dalton original protein size.

EXAMPLE 8

Protein Binding 5 ml of 5 mg/ml albumin in 0.1M $NaHCO_3$—NaOH, pH=9.2 was mixed with 2.0 mls of *vernonia* oil at 25° C. for 24 hrs, with constant stirring. The mixture was then chromatographed on a column of sephacryl 5200 equilibrated in 50 mM potassium phosphate, pH6.9, 100 mM NaCL. The protein peak was detected by UV adsorption, collected and rechromatographed to remove all traces of free *vernonia* oil. It is known that changing a protein by altering its size and surface characteristics by binding a molecule to it affects the protein's immunogenicity and half life.

It is often desirable to modify the release characteristics of small drugs in the body to obtain sustained or prolonged release. Again through the epoxide of vernonia oil it is possible to obtain base-catalysed (pH 8.0 to 10.0) bonding of small molecules containing amino, sulphydryl or hydroxyl (or other suitable nucleophilic) functions. A whole range of small molecules are feasible. Experiments with methotrexate indicate that bonding through the relatively inactive amino groups of that molecule occurs at pH 9.5. The covalent bonding appears to be one methotrexate molecule per triglyceride unit based on analysis.

EXAMPLE 9

Small Molecule Binding

Small molecule binding was achieved by mixing 10 ml of 3 mg/ml methotrexate buffered with 0.1M NaoH to pH 9.6 with 2.5 mls of *vernonia* oil prepared at 25° C. for 24 hrs with constant stirring. The mixture was then rotary evaporated to 3.5 mls and chromatographed on a column of Sephadox G-25 equilibrated in 0.1M $NaHCO_3$ pH 8.5. The second running and yellow peak representing *vernonia* oil coupled to methotrexate was then collected and rechromatographed to ensure purity. Mass spectral analysis indicated that the collected material comprised one methotrexate per triglyceride unit as an average linkage.

We claim:

1. A method of treating the skin of a mammal to ameliorate the symptoms of a skin disease or reduce a lesion on the skin comprising topically administering to the mammal an effective amount of *vernonia* oil obtained by extraction from *Vernonia galamensis* seed wherein said lesion is an ulcer, a wound, or caused by a skin disease, infection or inflammation, said skin disease being selected from psoriasis, dermatitis, or eczema.

2. The method as claimed in claim 1, wherein the wound is selected from a graze, a cut, a scratch and a burn.

3. The method as claimed in claim 1, wherein said *vernonia* oil contains oil, ester and wax, components of said oil, ester and wax, and mixtures thereof, all obtained from *Vernonia galamensis* seed.

4. A method for the prophylactic treatment of the skin of a mammal to reduce the recurrence of a lesion on the skin originally caused by a wound, a graze, a cut, a scratch, or a burn comprising topically administering to the site on the skin of the original wound, cut, scratch or burn, a composition comprising an effective amount of vernonia oil obtained by extraction from *Vernonia galamensis* plants.

5. The method of claim 1, wherein the vernolic oil contains vernolic acid.

6. The method of claim 4, wherein the vernolic oil contains vernolic acid.

* * * * *